Figures 1, 2:
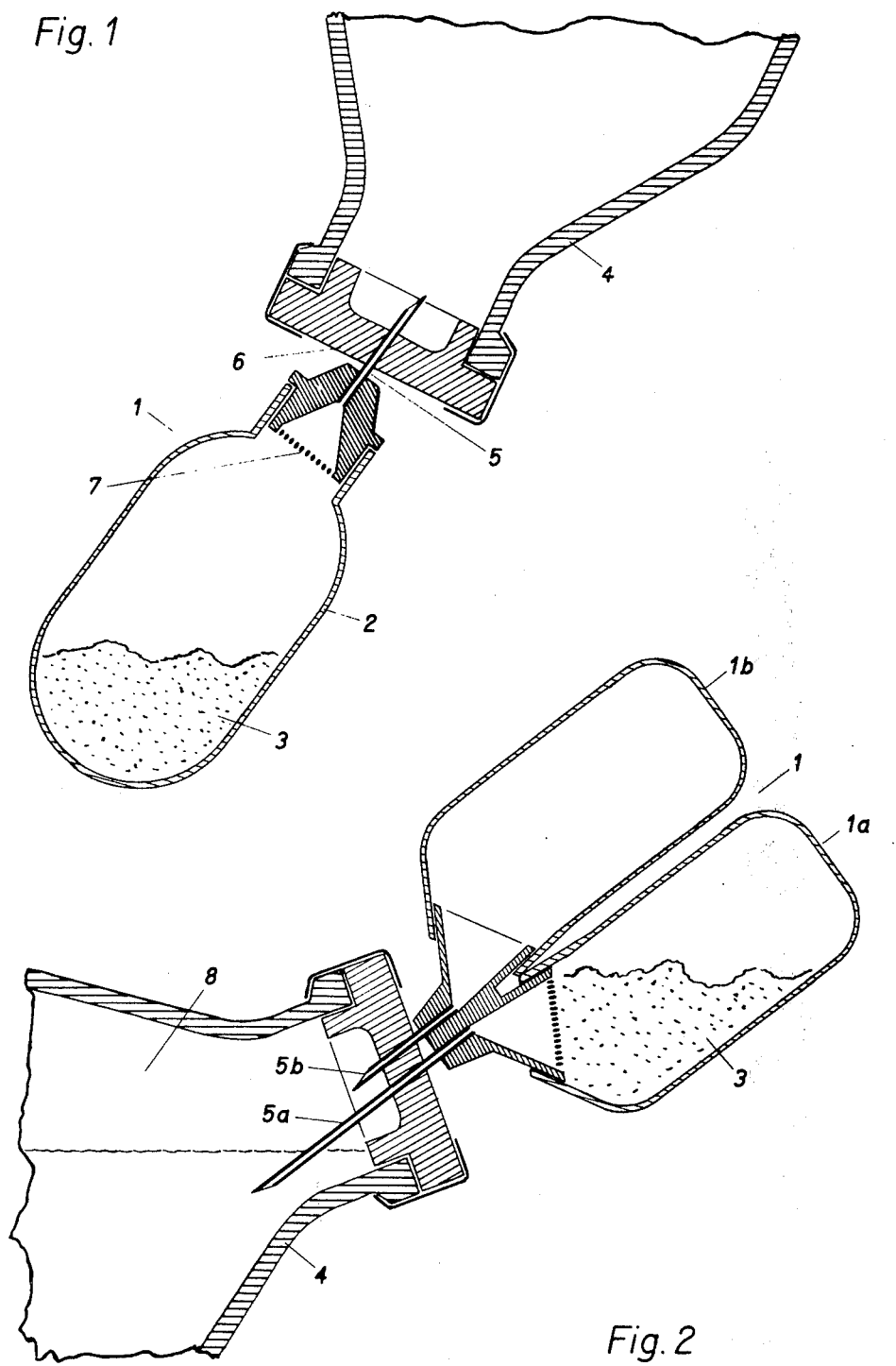

United States Patent [19]

Haury-Wirtz et al.

[11] 3,941,167
[45] Mar. 2, 1976

[54] ADMIXTURE AND PROCESS FOR THE PRODUCTION OF SOLUTIONS FOR INFUSIONS

[75] Inventors: Ingeborg Maria Haury-Wirtz, Schildgen; Lothar Otto Barensfeld, Bergisch Gladbach; George Edgar Callahan, Dusseldorf, all of Germany

[73] Assignee: Compaselect GmbH, Zug, Switzerland

[22] Filed: Jan. 2, 1974

[21] Appl. No.: 430,155

[30] Foreign Application Priority Data
Jan. 3, 1973 Switzerland.......................... 3573/73

[52] U.S. Cl.................. 141/1 R; 141/329; 141/104
[51] Int. Cl.² ......................................... B65B 3/04
[58] Field of Search ........... 141/329, 1, 9, 100, 104, 141/99, 25, 5–8, 2

[56] References Cited

UNITED STATES PATENTS 3,332,421  7/1967  King et al. .......................... 141/329

*Primary Examiner*—Houston S. Bell, Jr.
*Attorney, Agent, or Firm*—Larson, Taylor and Hinds

[57] ABSTRACT

Process and apparatus for mixing infusion liquids with further ingredients by adding the latter from a separate container in strongly concentrated or easily soluble ("instant") form, buffering agents being furthermore added to the ingredient to prevent variation of the pH value in the solution. The dissolution may be accelerated by several pumping to and fro operations between the infusion bottle and the container for the ingredient.

11 Claims, 2 Drawing Figures

U.S. Patent    March 2, 1976    3,941,167

ADMIXTURE AND PROCESS FOR THE PRODUCTION OF SOLUTIONS FOR INFUSIONS

The present invention relates to an admixture for mixing with liquids which have been filled into infusion bottles, a process for the production of ready-for-use solutions for infusions and rinsing and a mixing device for effecting the process.

It is generally known and usual nowadays to add to liquids in infusion bottles, before dispensing, additional substances, also called additives. Such additives are for example vitamins, medicaments improving blood circulation, antibiotics, medicaments for the liver, etc. A disadvantage of this procedure consists in that numerous such medicaments are not compatible with each other and/or with the liquid contained in the infusion bottle and cannot therefore be combined. Particularly, compatability strongly depends on the pH value of the solution ready for infusion; variations of the pH range may for example be the cause of precipitation and of losses in effectiveness. A further disadvantage consists in that additives in powder or paste form must be dissolved and/or diluted with a relatively big quantity of solvent and can then only be added to the infusion liquid. The consequence of this is frequently that the desired final concentration of the solution ready for infusion cannot be obtained because the so-called adding space of the infusion bottles is restricted. Furthermore, the required removal, mixing and adding steps always comprise the danger of contamination of the additives, their solvents and of the infusion liquids.

It is a purpose of the present invention to avoid the disadvantages of the known methods of producing infusion solutions and especially to simplify the precautionary measures, to rationalize the necessary working steps and furthermore to maintain the effectiveness of added additives.

According to the present invention, this is primarily achieved by adding to the additive at least one buffering agent and/or alkalizing or acidifying compound to obtain a predetermined pH range of the solution ready for infusion, and that the additive and the buffering agent are adapted, as far as their quantity and quality are concerned, to the volume and the pH range of the contents of the infusion bottle and have been prepared in the form of powder or paste which is soluble as well as possible. According to the present invention, the pH compatibility of the amixed ingredients is assured in a simple manner. Furthermore, the use of substances which up to now seemed unsuitable for infusion therapy and the composition of individual combinations of additives and liquids is rendered possible.

According to the present invention, it is provided that the user, for producing the infusion or rinsing solutions ready for use, at first dissolves the ingredients in a mixing device and then adds them to the infusion bottle. It is then especially recommendable, for complete or partial dissolution, to remove a part of the contents of the bottle, to mix the same with the ingredient and then to put it into the infusion bottle again.

The course of the process can be simplified in particular if, for removal of liquid, the mixing device and the infusion bottle are connected together to form a system closed from the outside and communicating with each other until the end of the adding procedure. In this manner the closed system prevents contamination of the ingredients and of the contents of the bottle, which could easily occur with separate removal, mixing and adding operations. It is advantageous, particularly with diffultly soluble ingredients, to pump back and forth at least twice the partial liquid quantities between the mixing device and the infusion bottle whereby residues which may have remained in the mixing vessel can be dissolved.

Simple removal of partial quantities from the infusion bottles is possible if the bottle is subject to pressure and the liquid thereby forced into the mixing device. This can be realized advantageously by providing a source of compressed air which provided the necessary pressure in the bottle as well as by at first pressing air into the infusion bottle from the mixing device thereby compressing the air reserve contained in the bottle. In both cases, upon release of the pressure, liquid is transported from the infusion bottle into the mixing vessel.

The mixing device itself preferably comprises a container the volume of which is variable which advantageously consists of elastically deformable material and furthermore comprises a connecting part, in particular a hollow needle which can be inserted by puncture into the sealing part of the infusion bottle and renders possible the exchange of ingredients.

The connecting part should, for reason of contamination, be fixed essentially and 'a priori' on the container. In certain cases, it is also possible to fix it later on, i.e., before use.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the concept upon which this disclosure is based may readily be utilized as a basis for the designing of other structures for carrying out the several purposes of the invention. It is important, therefore, that the claims be regarded as including such equivalent constructions as do not depart from the spirit and scope of the invention.

FIG. 1 of the drawings shows a mixing device; and
FIG. 2 of the drawings shows a modified form of a mixing device.

The invention will hereinafter be explained in more detail in examples as well as by means of the drawings.

EXAMPLE 1:

As basic infusion liquid, there is used 500 ml of an aqueous 5.5% D-glucose solution which has been filled in a usual 500 ml glass infusion bottle. Depending on the conditions of production, sterilisation and storage, the pH value of this sugar solution lies in the acid range of between 3.5 and 5. It is desired to add to this solution 500 mg of the antibiotic Novobiocin (corresponding to 700 mg of Novobiocin-sodium) which, however is not compatible with acid solvents, should precipitation and loss of effectiveness be avoided. It is desired to have a pH range of approximately between 7 and 8.

The mixing device contains, in sterile condition, 700 mg of Novobiocin-sodium as well as — for buffering of the solution ready for infusion to an admittable pH value — for example 500 mg of disodium hydrogen phosphate dihydrate and 800 mg of 2-amino-2-hydroxymethyl-1,3-propanediol, futhermore approximately 12 ml of sterile air. The volume of air is chosen so that it corresponds to at least the double of the liquid volume necessary for dissolution so sufficient overpressure is created in the infusion bottle even when handling it carelessly.

After puncture of the sealing part of the infusion bottle by means of a hollow needle fixed in the mixing container, the sterile air is at first pressed completely or to a large extent into the bottle and then, because of release of the created overpressure, liquid is transported from the bottle into the mixing device. After approximately 5 seconds, the substances have been dissolved and can now be injected into the contents of the bottle by pressing on the mixing container.

EXAMPLE 2:

Instead of a ready D-glucose solution of 5.5% the pH value of which lies within a relatively wide acid range, it is also possible to freshly prepare an analogous basic infusion liquid with a defined pH value by the following method. By means of one of the hereinafter described mixing devices, 27.5 g of sterilized and neutralized (or eventually adjusted to any other pH value) are brought, as explained and in a known manner into 500 ml aqua pro infusione in the form of D-glucose prepared as rapidly dissolvable dry substance ("instant"). Since buffering is not necessary, the 700 mg of Novobiocin-sodium may be added afterwards or previously without further substances.

A further simplification, namely the combination of two separate adding operations into one is possible by the mixing device containing 700 mg of novobiocin-sodium as well as 27.5 g of accordingly prepared glucose.

EXAMPLE 3:

For the production of amino acid infusion solutions which contain electrolytes and sugar, the amino acids and the electrolytes may be added to a sugar containing basic infusion liquid in several injection operations, or this may be preferably done with amino acids, electrolytes and sugar in dry and/or paste preparation together with the corresponding quantity of aqua pro infusione by means of the mixing device according the present invention. The problem in this case is the relatively very big need of dissolution water which renders impossible the addition of already dissolved compostions because the so-called adding space of the infusion bottles (difference between the nominal content) and the actually possible content is too small; in the normalized 500 ml infusion bottles, it is only approximately 70 ml. According to the invention, this problem is resolved by bringing the dry and/or paste substances prepared for rapid dissolution contained in the mixing device again and again into contact with less saturated liquid by several to and fro pumping operations and therefore successively dissolving them in the liquid (which is always present in the solutions ready for infusion) without essentially increasing the liquid volume in the infusion bottle.

For example, the mixing device for the production of an amino acid solution ready for infusion — related to 500 ml aqua pro infusione — contains the following substances prepared for the best possible solubility: as amino acids (always indicated in grams) 1.55 L-Arginin, 0.5 L-Histidin, 1.1 L-Leucin, 0.8 L-Lysin, 0.7 L-Isoleucin, 0.8 L-Valin, 1.1 L-Methionin, 1.1 L-Phenylalanin, 0.5 L-Threonin, 0.25 L-Tryptophan and 12.5 Glycin and additionally as electrolytes (always given in miniequivalents - mval) 20 Na+, 13K+, 2.5 Mg++, and 18 l actate-. As energizer, furthermore, a neutralized and instantized sugar composition is contained, for example correspondingly prepared D-fructose in a quantity of 50 g. It is true that it is thought unsuitable to combine amino acids with such reducing sugar compositions because, during sterilizing as well as during prolonged storage of the solutions the amino acid — amino groups may react with the aldehyde or keto group of the sugar compositions and thereby not only produce brownish discolouration, but also form by-products which are not indifferent biologically. Neutralizing of the mixture of amino acids is effected by the anion excess which in this case is 12.5 mval.

After dissolution of 500 ml of aqua pro infusione by approximately 12 to and fro pumping operations, the solution is ready for infusion; its pH value is 7.

The above described mixing operation may be effected with the usual syringes or injection phials as well as particularly advantageously with the subsequently described mixing devices.

The mixing device of FIG. 1 is characterized by particular ease of operation. The wall 2 of the container 1 consists of elastically deformable, preferably transparent material, for example synthetic plastic material so that, by compression of container 1, the sterile air present in the container can be forced into the infusion bottle 4. Upon release of the overpressure in the infusion bottle 4, liquid passes through the hollow needle 5 which has been passed through stopper 6 and into container 1. The mixing operation of the partial liquid quantity removed in this manner with the ingredient 3 may if necessary be accelerated or completely effected by several to and fro pumping operations between the mixing container 1 and the infusion bottle. The sieve insert prevents undissolved ingredient 3 from passing into the infusion bottle.

FIG. 2 shows a modified example in which the mixing container 1 comprises, in addition a single container 1a for containing the ingredient 3, an air filled container 1b for the creation of overpressure in the infusion bottle 4. As shown, the containers 1a and 1b are thus provided with hollow needles 5a and 5b so that overpressure is only created by the container 1b in the adding space without the possibility of evacuation of liquid by suction. Before insertion of the needles 5a, 5b, the air contained in container 1a is at first partially removed by compression of container 1a. Since the hollow needle 5a extends below the liquid level in the infusion bottle 4, compression of container 1 presses liquid into container 1a. The ingredient 3 is thus dissolved and is passed back into the infusion bottle 4 after release of container 1a, 1b and compression of container 1b. With a corresponding volume of the containers 1a and 1b, it is also possible to pass liquid into container 1a only by compression of container 1b, without previously pressing out air.

Instead of the resilient containers 1a, 1b, containers of non-resilient deformable material, for example of synthetic resins, can be provided. For example, it is advantageous if the containers 1a, 1b are made replaceable by conventional syringe containers and are connectable by means of the intermediate portion with the two needles 5a, 5b.

In this case, it is of course also possible, instead of using two separate needles, to utilize a needle with two channels which in this case advantageously comprise different openings. It is also possible to provide a needle with an air evacuating channel for pressure release during injection.

We believe that the construction and operation of our novel apparatus and process will now be understood, and that the advantages of our invention will be fully appreciated by those persons skilled in the art.

We claim:

1. In a method of preparing a ready-for-use bottle of infusion or rinsing solution in which the solution is prepared for use by adding at least one additive to a previously prepared bottle of infusion or rinsiing solution, the improvement comprising providing the additive in powder or paste form in a quantity adapted to the quantity of the solution in said bottle and having a quality adapted for compatability with the solution in said bottle in a variable volume container, the volume of said variable volume container being larger than that occupied by the additive in said variable volume container, and adding said additive to said bottle by introducing a portion of the solution from said bottle into said variable volume container, mixing the additive and solution in said variable volume container and introducing the mixture from said variable volume container into said bottle.

2. An improved method according to claim 1 wherein introduction of solution into said variable volume container is effected by passage through a tube extending between said bottle and said variable volume container and forming therewith a sealed fluid communication system.

3. An improved method according to claim 2 wherein introduction of said mixture into said bottle is effected by passage through said tube.

4. An improved method according to claim 2 wherein introduction of said mixture into said bottle is effected by passage through a further tube extending between said variable volume container and said bottle and forming therewith a sealed fluid communication system.

5. An improved method according to claim 2 wherein passage of said solution through said tube is motivated by first introducing air through said tube by reducing the volume of said variable volume container and utilizing the overpressure thus produced in said bottle to force solution from said bottle to said variable volume container.

6. An improved method according to claim 3 wherein said mixture is introduced into said bottle by reducing the volume of said variable volume container.

7. An improved method according to claim 4 wherein said mixture is introduced into said bottle by reducing the volume of said variable volume container.

8. An improved method according to claim 1 wherein said mixture is added to said bottle by squeezing said variable volume container which includes a resilient wall.

9. An improved method according to claim 1 wherein said mixture is added to said bottle by squeezing said variable volume container which comprises a plastic squeeze bottle.

10. An improved method according to claim 9 wherein said mixture is added to said bottle by flowing through a hollow needle provided on said container for placing said bottle and container in fluid communication.

11. An improved method according to claim 9 wherein mixing is effected by repeatedly pumping liquid between said container and said bottle by repeatedly squeezing said bottle.

* * * * *